United States Patent [19]

Saumade et al.

[11] Patent Number: 4,806,850
[45] Date of Patent: Feb. 21, 1989

[54] METHOD AND APPARATUS FOR ANALYZING THE CORROSIVE EFFECT OF THE SOIL AND ITS ENVIRONMENT ON A BURIED METALLIC STRUCTURE AND THEIR APPLICATION TO THE LOCATING OF SAID EFFECT

[75] Inventors: Frank Saumade, Plaisir; Guy Fontaine, Paris, both of France

[73] Assignee: Compagnie de Raffinage et de Distribution Total France, Paris, France

[21] Appl. No.: 948,026

[22] Filed: Dec. 31, 1986

[30] Foreign Application Priority Data

Dec. 31, 1985 [FR] France .................................. 85 19501

[51] Int. Cl.4 ...................... G01R 27/02; G01N 27/00
[52] U.S. Cl. ................................. 324/71.1; 324/65 CR
[58] Field of Search ...................... 324/71.1, 71.2, 72, 324/65 CR; 364/420, 496, 505–507; 204/1 C, 1 T, 404

[56] References Cited

U.S. PATENT DOCUMENTS

| | | | |
|---|---|---|---|
| 2,803,797 | 8/1957 | Cowles | 204/404 |
| 2,862,177 | 11/1958 | Titterington | 324/72 |
| 2,974,276 | 3/1961 | Davis | 324/72 |
| 3,660,249 | 5/1972 | Townsend | 324/71.2 |
| 3,893,026 | 7/1975 | Glazkov et al. | 324/72 |
| 3,999,121 | 12/1976 | Taylor, Jr. | 324/65 CR |
| 4,051,436 | 9/1977 | Weir, Jr. | 204/404 |
| 4,151,458 | 4/1979 | Seager | 324/72 |
| 4,155,814 | 5/1979 | Tejfalussy et al. | 204/404 |
| 4,322,805 | 3/1982 | Rog et al. | 364/420 |
| 4,481,474 | 11/1984 | Gerrit | 324/65 CR |
| 4,584,430 | 4/1986 | Nicholson | 324/72 |
| 4,584,430 | 4/1986 | Nicholson | |
| 4,611,175 | 9/1986 | Kumat et al. | 324/65 CR |

FOREIGN PATENT DOCUMENTS

| | | |
|---|---|---|
| 1191899 | 8/1985 | Canada . |
| 2707265 | 8/1978 | Fed. Rep. of Germany . |
| 1342949 | 1/1974 | United Kingdom . |
| 2025056 | 1/1980 | United Kingdom . |
| 2049943 | 12/1980 | United Kingdom . |

OTHER PUBLICATIONS

Charpentier et al. IBM Technical Disclosure Bulletin vol. 26, No. 4, Sep. 1983 pp. 2020–2021 "Electrochemical Cell . . . ".

Primary Examiner—Parshotam S. Lall
Assistant Examiner—S. A. Melnick
Attorney, Agent, or Firm—A. Thomas S. Safford

[57] ABSTRACT

The invention relates to the continuous or discontinuous analysis of the corrosive effect of the soil and the environment on a buried metallic structure (such as an underground gasoline storage tank for retail gas stations). The apparatus includes a measuring system having a sensor with at least one $Cu/CuSO_4$ electrode to which a metallic electrode containing iron is secured at least one voltmeter, and optionally at least one current generator; at least one data display and acquisition system consisting of at least one amplifier, at least one analog-to-digital converter, at least one magnetic recorder and at least one display unit for the read-out of these data on the site, these belonging to the group formed by the numerical display devices and the electromechanical recorders; and a system for the processing of these data consisting of data-processing computing means.

20 Claims, 7 Drawing Sheets

METHOD AND APPARATUS FOR ANALYZING THE CORROSIVE EFFECT OF THE SOIL AND ITS ENVIRONMENT ON A BURIED METALLIC STRUCTURE AND THEIR APPLICATION TO THE LOCATING OF SAID EFFECT

The present invention relates to a method for analyzing the corrosive effect of the soil and its environment on a buried metallic structure and to its application to the locating of said effect. The invention further relates to an apparatus for carrying out said method and said application.

Buried metallic structure here means any underground metallic infrastructure of the type of service-station piping and tanks, domestic-fuel tanks or storage tanks and any transportation or distribution system for organic and mineral fluids in liquid or gaseous form.

It is known that buried metallic structures corrode through the formation of electric cells on their surface, the corrosion developing in the anodic zones of these cells. The formation of such cells is dependent on at least two factors: The heterogeneity of the soils traversed by the structure, and the metallic composition of the latter. Moreover, the presence of stray currents coming from external sources located in the environment of the structure also causes corrosion.

The metallic composition of the structure can be controlled, insofar as the material of which the structure is made is known before it is buried, but the heterogeneity of the soil and the presence of stray currents cannot. In particular, it is difficult to know from the surface of the soil the quality of the soil traversed by the structure, millimeter for millimeter. All it takes is for a rock, a block of wood, or humus to come in contact with the surface of the structure, which is already in contact with a material differing from it with respect to its nature, its acidity, its density, its grain size or its moisture, for a cell effect to occur at the level of the block, the rock or the humus, the cell generally forming at the boundary of two dissimilar materials on the surface of the structure.

In seeking to detect from the surface of the soil the corrosive effect of the latter and of the environment on a buried structure, it is customary to carry out a point-to-point measurement of three characteristics directly above the structure being examined, namely:

The difference in potential between the soil surface and the buried structure, measured with a voltmeter between a reference electrode of the $Cu/CuSO_4$ type, whose sensitive portion is placed in contact with the surface of the moistened soil, and a valve, for example, connected to the buried structure and emerging from the soil surface;

the resistivity of the soil, measured by the so-called "Wenner bridge" method in accordance with a known technique; and the pH, measured by core sampling of the soil in the vicinity of the buried structure.

Comparison of the average values of these measurements, made at more or less regular intervals of at least one meter, for these parameters, and of values generally regarded as indicating a significant corrosive effect of the soil or its environment, will then make it possible to decide whether or not to apply cathodic protection to the structure.

This procedure for detection of the corrosive effect of the soil and its environment makes it possible to find out whether the latter on the whole are corrosive or not, but not to pinpoint the anodic areas where corrosion is setting in, nor to determine the size of these areas. Besides, regardless of the decision made on the basis of the results obtained by carrying out this procedure, the consequences thereof are or will be very costly: It will always be necessary sooner or later to apply cathodic protection or to unearth the structure in order to look for the "holes" resulting from corrosion, which are difficult if not impossible to locate from the soil surface by this approach.

The present invention seeks to provide a reliable corrosion-detection method whereby areas which are corroded or are susceptible to being corroded and their extent on the buried structure can be pinpointed and the corrosive effect of the soil or its environment on the structure can be quantified.

To this end, it is proposed, contrary to the procedure employed in the prior art, to monitor by means of continuous or semicontinuous measurements between the soil surface and the buried structure the quasicontinuous development of parameters such as the differences in potential between the buried structure and the soil surface, and the resistivity of the soil in the vicinity of the structure. Interpretation of these developments makes it possible in fact to determine the direction and intensity of the current at the level of the cell formed on the surface of the structure, the leaving current indicating the presence of an anodic area susceptible to corrosion.

The present invention thus has as an embodiment a method of analyzing continuously or discontinuously the corrosive effect of the soil and its environment on a buried metallic structure which is characterized by the following operations:

(A) The measurement of at least two potential differences by means of at least one known reference-potential electrode placed in contact with the surface of the soil, the latter then forming the electrolyte and the buried structure forming a metallic electrode, these potential differences being:

A potential difference $V_1$, between the soil surface and the buried structure, that is equal to the sum of the potentials of the known reference-potential electrode, the "buried-structure" electrode, and a potential difference generated by the action of the electric exchange occurring between the structure and the soil;

a potential difference $V_2$, between the soil surface and the buried structure, when the potential of that structure is returned, by means of an electric connection, to a metallic electrode resting on the ground, this difference being equal to the sum of the potentials of the known reference-potential electrode and the metallic electrode;

and, optionally, at least a third potential difference $V_3$, between the soil surface and the buried structure, made up like $V_1$ but obtained by modifying the potential difference generated by the action of the electric exchange occurring between that structure and the soil;

(B) The display and recording of these potential differences with a data display and acquisition unit.

(C) The processing of these data with data-processing means for computation of the differences $(V_1-V_2)$, optionally by the use of a difference $(V_3-V_1)$; and (D) Determination on the basis of these potential differences of the corrosive effect of the soil and the environment on the buried structure.

For measurement of the potential difference V1, the known reference-potential electrode, preferably a Cu/CuSO$_4$ electrode, may be placed vertically over the point concerned on the buried structure.

For measurement of the potential difference V2, the metallic electrode returning the potential of the structure to the ground may be joined to the known reference-potential electrode of Cu/CuSO$_4$, for example, and the two may be placed on the ground at a distance d$_2$ on the ground from the vertical of the point cncerned on the structure, d$_2$ being preferably between 0 and 50 cm. This arrangement of the two electrodes relative to each other would have the advantage of eliminating or minimizing the effect tied to the electric exchange between the soil and the structure.

For measurement of the potential difference V3 in accordance with the invention, the potential difference of the electric exchange between the soil and the buried structure can be modified by manipulating one of the two parameters which make up this potential difference, that is, the intensity of the exchange current between the structure and the soil or the resistance of the soil between the soil surface and the buried structure.

In accordance with a preferred mode of carrying out this method, for modification of the intensity of the exchange current between the structure and the soil, at least one electric current can be generated between the referencepotential electrode, such as a Cu/CuSO$_4$ electrode, and the electrode formed by the buried structure.

For modification of the soil resistance, the Cu/CuSO$_4$ electrode may be shifted on the ground by a distance d$_3$ from the vertical of the point being analyzed of the structure, d$_3$ ranging preferably from 50 to 200 cm, and V3 measured like V1 between the Cu/CuSO$_4$ electrode and the "buried-structure" electrode.

The present invention has as a further embodiment an apparatus for carrying out the method, characterized in that it comprises:

A measuring system consisting of a sensor comprising at least one Cu/CuSO$_4$ electrode to which a metallic electrode containing iron is secured, at least one voltmeter, and optionally at least one current generator;

at least one data display and acquisition system consisting of at least one amplifier, at least one analog-to-digital converter, at least one magnetic recorder and at least one display unit for the read-out on site of these data, these belonging to the group formed by the numerical display devices and the electromechanical recorders; and a system for the processing of these data consisting of data-processing computing means.

Two designs of the sensors which form part of said measuring system are regarded as preferred. These are, on the one hand, the linear-development sensors, which are in permanent contact with the soil, providing for the continuous measurement of the potential differences V1 and V2, and optionally at least V3, and, on the other hand, the point-to-point development sensors, lifted off the ground from one measurement to the next and giving only discontinuous measurements of these potential differences.

The linear-development sensors in accordance with the invention comprise at least two Cu/CuSO$_4$ electrodes in the form of hollow wheels, X1 and X2, whose periphery forms the sensitive portion of the electrode and is made of a material selected from the group consisting of cork, wood and, more generally, any porous, electrically passive material. The side walls, in the form of disks, of these wheels are made of an electrically passive, nonporous material containing a copper disk of a diameter smaller than that of the wheel and a saturated solution of copper sulfate, CuSO$_4$. The electrodes X1 and X2 are arranged in parallel and maintained integral with each other, X2 at a distance d$_2$ from X1. The sensor may optionally comprise also at least a third Cu/CuSO$_4$ electrode, located at a distance d$_3$ from X1. The sensor finally comprises at least one metallic electrode, preferably of low-carbon steel, formed of at least one metallic disk, optionally joined to one of the Cu/CuSO$_4$ electrodes X1, X2 or X3.

It will be obvious to one skilled in the art that this type of linear-development sensor may comprise more than three Cu/CuSO$_4$ electrodes and more than one metallic electrode to permit other potential differences between the soil surface and the structure to be measured.

The point-to-point development sensors in accordance with the invention may comprise on the one hand at least one Cu/CuSO$_4$ electrode obtained from a cylinder of electrically passive, nonporous material that is stoppered at its base by a plug of a porous material selected from the group consisting of wood, cork or, more generally, any other porous, electrically passive material, said cylinder containing a saturated solution of copper sulfate, CuSO$_4$, into which a copper rod dips to provide for electrical connection of said electrode, and, on the other hand, a metallic electrode enveloping the Cu/CuSO$_4$ electrode with a metallic sheath, preferably of low-carbon steel. For the measurement of different potentials, and particularly of V1 and V3, the point-to-point development sensor may be raised, if there is only one, to shift it, this sensor then only furnishing discontinuous measurements.

When the ground is flat and free of obstacles, it will be more advantageous to use a linear-development sensor as it requires less physical effort on the part of the operator who performs the analysis and provides a picture of the development of the potential differences V1, V2 and optionally at least V3 all along the structure without skipping a surface element thereof.

However, when the topography of the ground is rougher, for example, when a distribution or transportation conduit traverses the soil of a forest, linear-development sensors will run with difficulty because of the obstacles encountered. In this case, the use of the point-to-point development sensor is more practical.

The data display and acquisition system selected is preferably portable so it can be transported to the site and be permanently connected with the sensor for the purpose of monitoring the development of the potential differences V1, V2 and optionally at least V3.

On the other hand, the data-processing computing means making up the data-processing system may be mobile, like most of the microcomputers, or stationary, as certain mainframes.

The function of this data-processing system in accordance with the invention is to re-read the data V1, V2 and optionally at least V3 recorded on the site by means of the data display and acquisition system, to standardize the values of V1, V2 and optionally at least those of V3 on the basis of the real potentials of the Cu/CuSO$_4$ electrodes used which are known, and to compute the difference (V1−V2), optionally the difference (V1−V3), and any other differences in potential difference relative to V1.

These differences are utilized to locate and quantify, at least relatively, the intensity of the corrosive effect of the soil and the environment on the buried structure.

The present invention has a further embodiment the application of this method and of this apparatus for analyzing the corrosive effect of the soil and its environment on a buried metallic structure to the locating on the site of anodic areas susceptible to corrosion, said application being characterized by the following operations:

Moving the sensor or sensors of the measuring system continuously or discontinuously along the buried structure on the ground, which has first been moistened to assure contact between sensor and soil;

reading the values of V1 and V2 on the display unit of the measuring system; and locating and indicating the anodic areas when the absolute value of V1 is higher than that of V2.

Other characteristics and advantages of the invention will become apparent from the detailed description which follows of certain embodiments, given by way of example but not of limitation. That description makes reference to the accompanying diagrammatic drawings, wherein.

Figure 1:
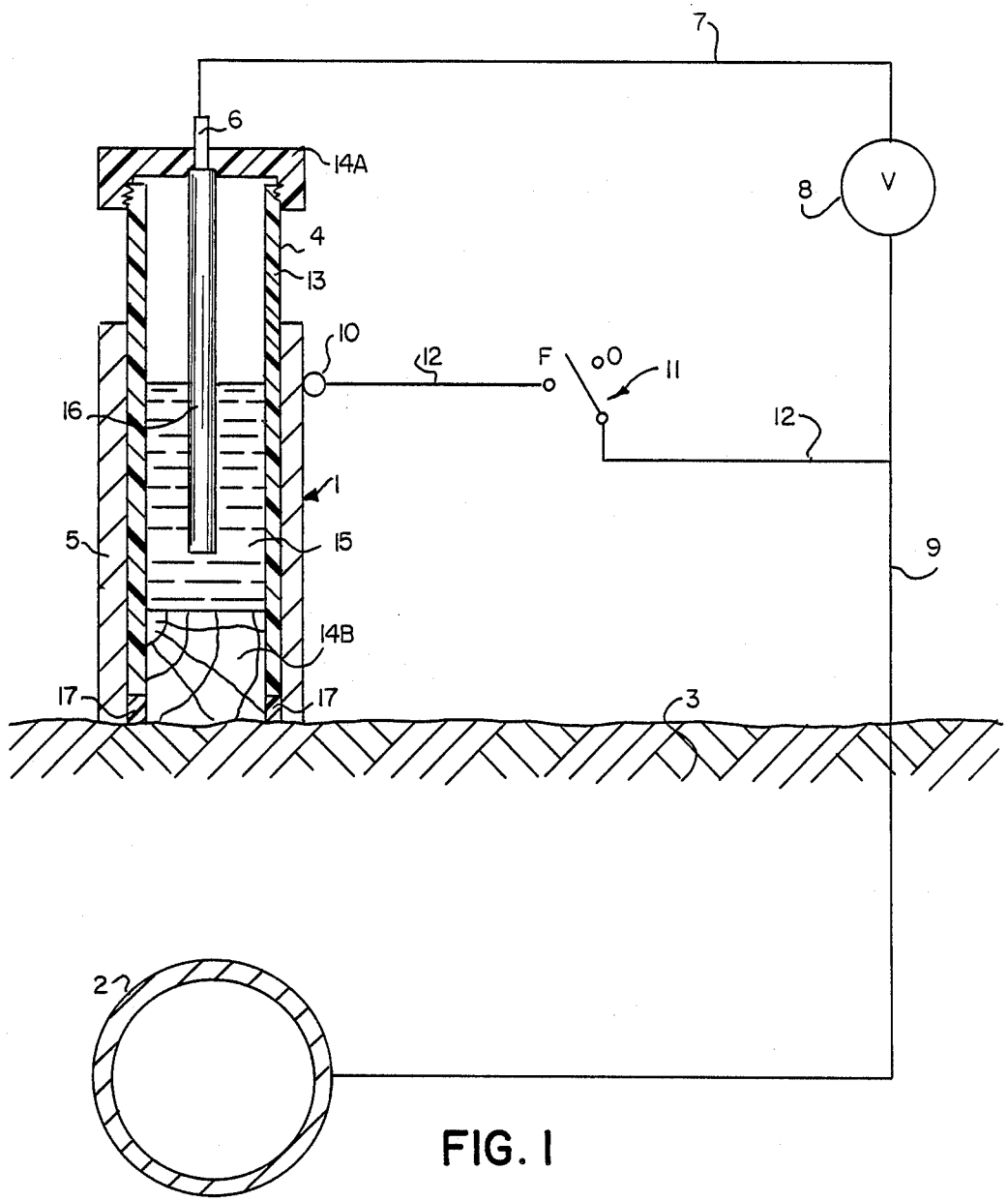
FIG. 1 shows a measuring means comprising a point-to-point development sensor positioned above a buried metallic pipe.

Reference will first be had to FIG. 1. The point-to-point development sensor 1 is positioned on the ground 3 vertically above the buried metallic pipe 2.

The sensor 1 consists of a Cu/CuSO$_4$ electrode 4 of cylindrical shape and of a metallic electrode 5 of steel which envelops the electrode 4 with a sheath 4 mm thick up to three quarters of its height. The sensor 1 is connected through the contact 6 of the electrical 4 and the electrical connection 7 to the voltmeter 8, which in turn is connected through the electrical connection 9 to the pipe 2 by way of a valve, not shown in the drawing, which emerges from the soil surface 3. The sensor 1 is likewise connected to the pipe 2, through the contact 10 of the electrode 5, which is connected to the switch 11 through the electrical connection 12, which leads to the electrical connection 9 between the voltmeter 8 and the valve.

The cylindrical wall 13 of the Cu/CuSO$_4$ electrode is formed of an electrically passive material, for example, polyvinyl chloride. It is stoppered at its upper end by an insulated plug 14A, of a nature comparable to that of the cylindrical wall 13, and at its lower end, the sensitive portion of the electrode 4, by a wooden plug 14B which slightly projects from the cylinder 13. This electrode further contains a saturated solution 15 of copper sulfate. CuSO$_4$, in which a copper rod 16 is immersed that passes through the plug 14 and forms at its upper end the contact 6 of the sensor 1.

The metallic envelope forming the electrode 5 projects from the cylindrical wall 13 of the electrode 4 by the same amount as the plug 14B, the circular cavity 17 between the plug 14B and the electrode 5 being filled with an electrically passive substance, for example, araldite.

For measuring V1 or V2, the sensor 1 is positioned on the moistened ground 3 above the pipe 2. The voltmeter 8 will indicate the potential difference V1 when the switch 11 is in the OPEN position (O), and the potential difference V2 when the switch 11 is in the CLOSED position (F). To measure V3, the sensor 1 is moved a distance $d_3$ on the ground so that it is no longer vertically above the pipe 2, and the switch is open (O).

Figure 2A:
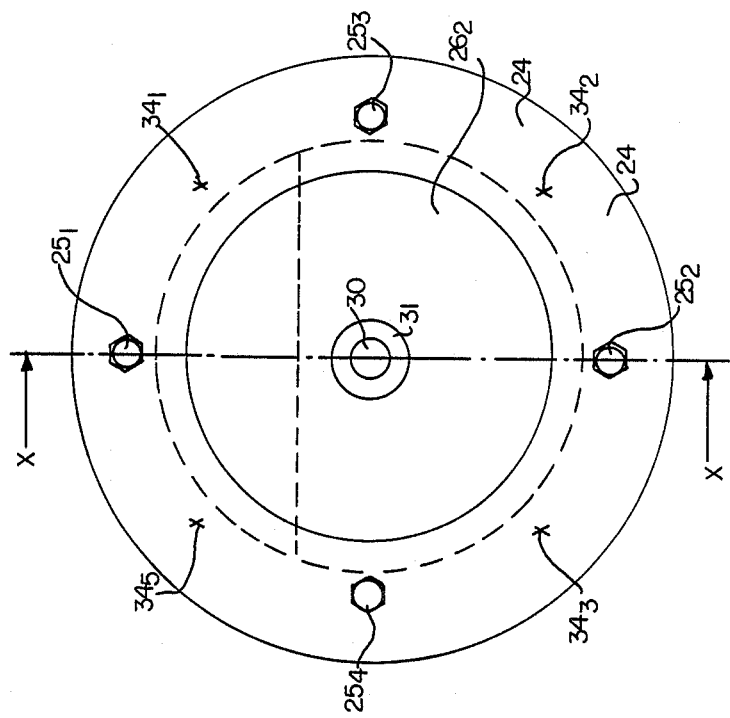
FIGS. 2A and 2B are a side elevation of a circular Cu/CuSO$_4$ electrode to which the metallic electrode is joined and a sectional view taken along the line X—X in FIG. 2A, respectively.
Figure 2B:
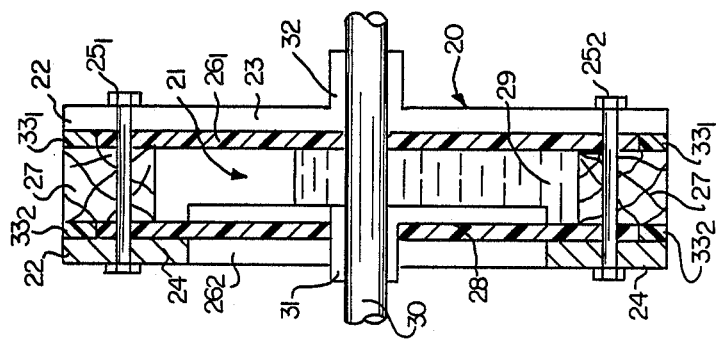

In the sensor 20 of FIGS. 2A and 2B, the Cu/CuSO$_4$ electrode 21 is circular and has the shape of a wheel 318 mm in diameter, and it is joined to a metallic electrode 22 of low-carbon steel, made up of a low-carbon steel disk 23 of the same diameter as the wheel forming the electrode 21 and 5 mm thick, and of a flat ring 24 of the same outside diameter and the same thickness as the disk 23, its inside diameter being 200 mm. Four steel bolts $25_1$, $25_2$, $25_3$ and $25_4$ serve as contacts between the disk 23 and the ring 24.

The Cu/CuSO$_4$ electrode 21 comprises two parallel circular walls $26_1$ and $26_2$ of a diameter of 310 mm and a thickness of 3 mm of an electrically passive material, which here is TECHNYL (a registered trademark). These walls $26_1$ and $26_2$ are maintained parallel by a layer of wood 25 mm wide and 25 mm thick, which is disposed at the periphery of these walls and forms the sensitive portion 27 of the Cu/CuSO$_4$ electrode that is constantly in contact with the soil. This sensitive portion 27 projects from the walls $26_1$ and $26_2$ by an amount of 4 mm.

In the interior of the wheel forming the Cu/CuSO$_4$ electrode 21, a copper disk 28 of a diameter equal to the inside diameter of the ring 24 is placed in contact with the wall $26_2$ and dips into a saturated solution 29 of copper sulfate, CuSO$_4$, which fills the wheel to the extent of two thirds.

The two electrodes are traversed at their center by an electrically insulated shaft 30, made of TECHNYL, for example, of a diameter of 20 mm and a length of 100 mm, this shaft serving as axis of rotation of the sensor 20.

The wall $26_2$ is pierced by a hole of a diameter greater than the diameter of the shaft 30 in order to permit the passage of a copper cylinder 31 whose inside diameter is the same as that of the shaft 30 and which is connected to the disk 28 to provide the Cu/CuSO$_4$ electrode 21 with an electrical contact on its exterior.

The disk 23 of electrode 22 which is secured to the wall $26_1$ of the Cu/CuSO$_4$ electrode 21 is pierced by a hole of the same diameter as that of the shaft 30, the same as wall $26_1$. At this level, the electrode 22 is provided with an electrical contact by a metallic cylinder 32 that is connected to the disk 23 and whose inside diameter is equal to the diameter of the insulated shaft 30. The grooves $33_1$ and $33_2$ are filled with araldite.

In FIG. 2A, the sensor 20 is seen from the side of wall $26_2$ of the copper/CuSO$_4$ electrode 21. The ring 24 is seen to be pierced by eight holes, which are filled by four low-carbon steel bolts $25_1$, $25_2$, $25_3$ and $25_4$ and four nylon bolts $34_1$, $34_2$, $34_3$ and $34_4$. The wall $26_1$, pierced at the center by a hole, permits the passage of the copper contact cylinder 31 of the Cu/CuSO$_4$ electrode 21 and of the insulated shaft 30.

Figure 3:
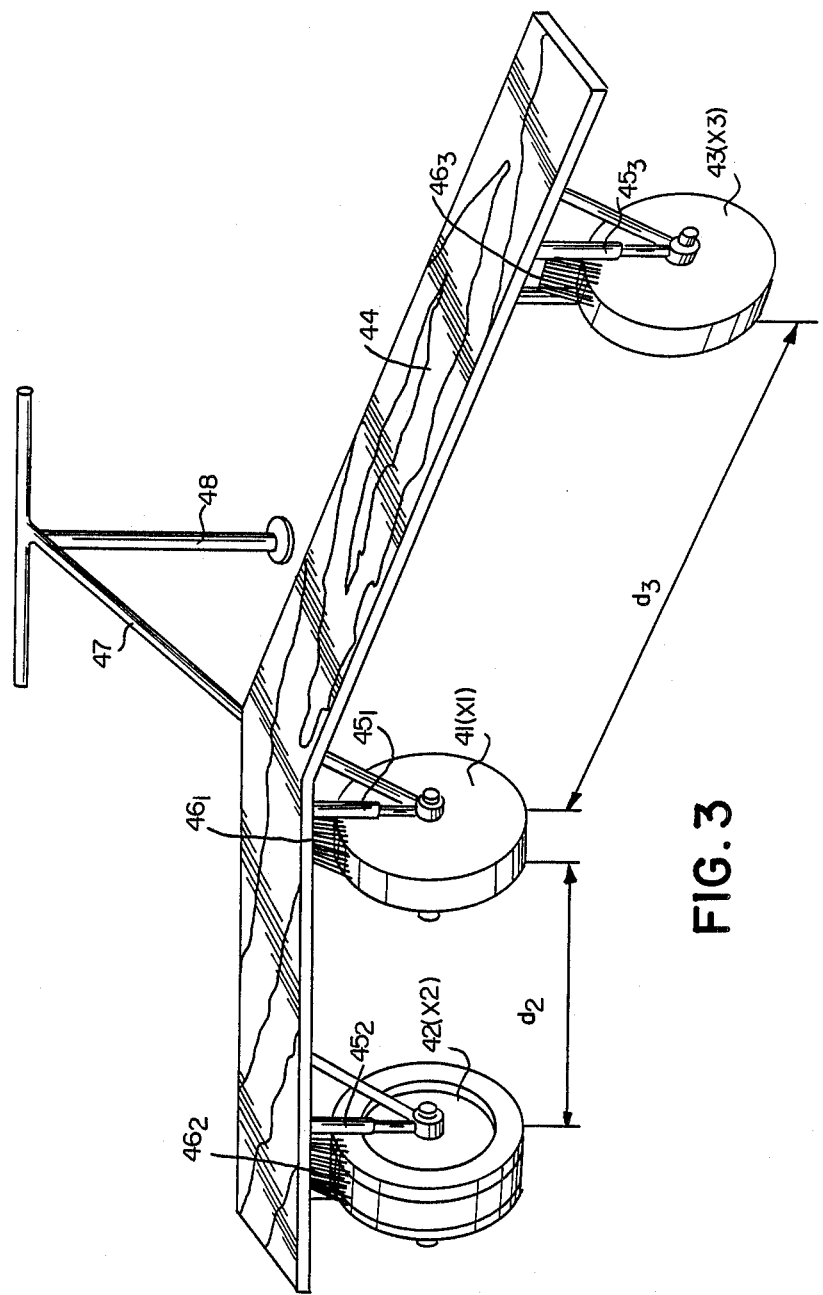
FIG. 3 shows a linear-development sensor comprising three circular electrodes X1, X2 and X3 and a metallic electrode.

The linear-development sensor of FIG. 3 consists of three wheels 41, 42 and 43 which correspond to the electrodes $X_1$, $X_2$ and $X_3$, $X_2$ comprising a metallic electrode secured to the Cu/CuSO$_4$ electrode, these three electrodes being maintained parallel by the use of a chassis 44 consisting of two wooden planks joined to the axles of the wheels by means of bars. In this sensor, $d_2$ is equal to 30 cm and $d_3$ is equal to 1 meter.

Dual shock absorbers $45_1$, and $45_2$ and $45_3$ are disposed at the level of the three wheels 41, 42 and 43 for the purpose of smoothing out the slight roughness of the ground.

To keep the sensitive portion of the Cu/CuSO$_4$ electrodes and of the metallic electrode clean at all times and free from waste or pebbles, small brooms $46_1$, $46_2$ and $46_3$ are placed under the planks of the chassis 44 so that they will sweep these sensitive portions when the sensor is rolling.

The sensor further comprises a T-shaped handle 47 that is secured to the chassis and permits the sensor to be steered. A stand 48 is welded to that handle for keeping the sensor straight in the rest position.

Figure 4A:
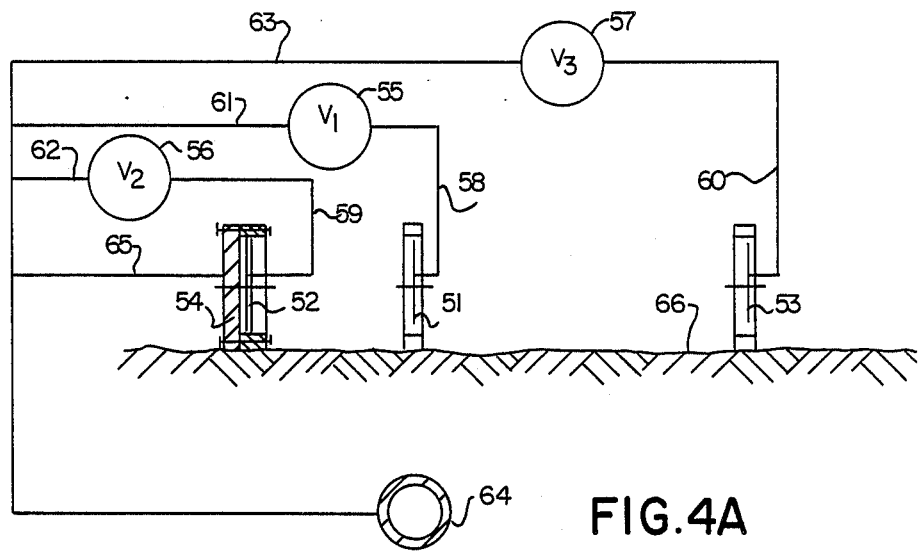
FIGS. 4A and 4B show two linear sensors permitting continuous measurements of V1, V2 and V3 to be made according to whether the soil resistance is modified (FIG. 4A) or the current intensity is modified by generation of an alternating current (FIG. 4B)

The linear sensor of FIG. 4A has only three Cu/CuSO$_4$ electrodes, 51, 52 and 53, and a metallic electrode 54 secured to electrode 52, all located on the ground 66. This sensor is connected to three voltmeters 55, 56 and 57, respectively, through electrical connections 58, 59 and 60 coming from the electrical contacts of the copper of electrodes 51, 52 and 53.

The second terminal of the voltmeters 55, 56 and 57 is connected through electrical connections 61, 62 and 63 to the buried pipe 64, disposed vertically below the electrode 51, by way of a valve emerging at the soil surface and not shown in the figure. The electrical connection 65 connecting the metallic electrode 54 to the valve permits the potential of the pipe 64 to be returned to ground level in proximity to the Cu/CuSO$_4$ electrode 52.

This sensor permits the continuous measurement of the three potential differences V1, between the pipe 64 and the electrode 52, V2, between the two electrodes 54 and 52, and V3, between the electrode 53 and the pipe 64.

Figure 4B:
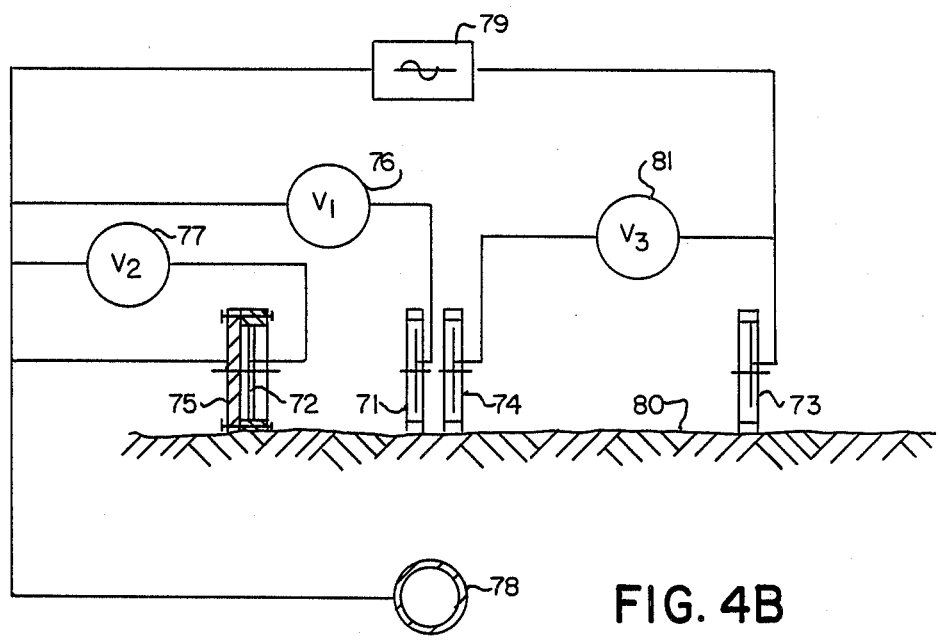

The linear sensor of FIG. 4B consists of four Cu/CuSO$_4$ electrodes, 71, 72, 73 and 74, and a metallic electrode 75 secured to electrode 72, all located on the ground 80. The voltmeter 76, connected to electrode 71 and to a valve that is connected to the pipe 78, and the voltmeter 77, connected to electrode 72 and to electrode 75, permit, as in the preceding figure, the measurement of V1 and V2.

For measuring V3, it has been decided to generate an alternating current. In this sensor, the electrode 73 has therefore been connected to an alternating-current generator 79, which in turn is connected to the pipe 78 by way of the valve, not shown in the figure. V3 is measured by a voltmeter connected to electrode 73 and electrode 74 and located at a distance of 600 mm from electrode 71.

As with the preceding sensor, V1, V2 and V3 can be measured continuously when the sensor rolls over the ground above the buried pipe.

Figure 5:
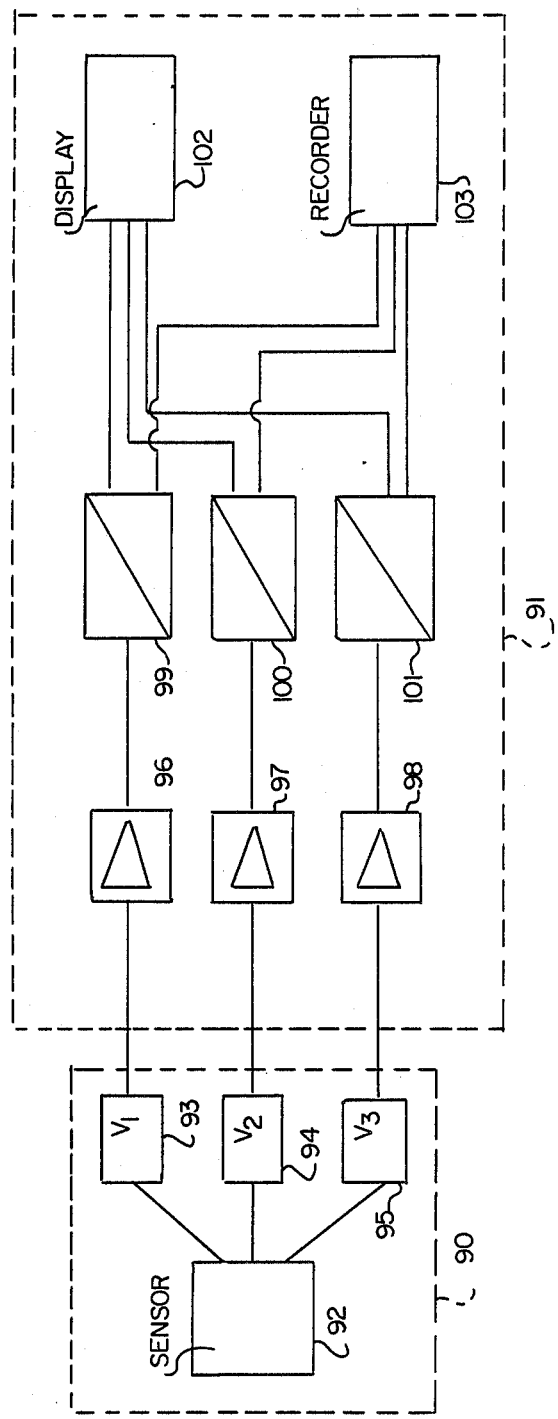
FIG. 5 is a diagram of the functions of the measuring system associated with the data display and acquisition system.

In FIG. 5, the block 90 represents the measuring system, which consists of the sensor 92 and at least the three voltmeters 93, 94 and 95. These three voltmeters are connected to three amplifiers 96, 97 and 98, respectively, of the data display and acquisition system 91, which in turn are connected to analog-to-digital converters 99, 100 and 101. These converters are connected to a display unit 102 formed by numerical indicators permitting the values V1, V2 and V3 to be read on the site when the sensor is rolled or displaced, and to a magnetic recorder 103 permitting these data to be stored.

Figure 6:
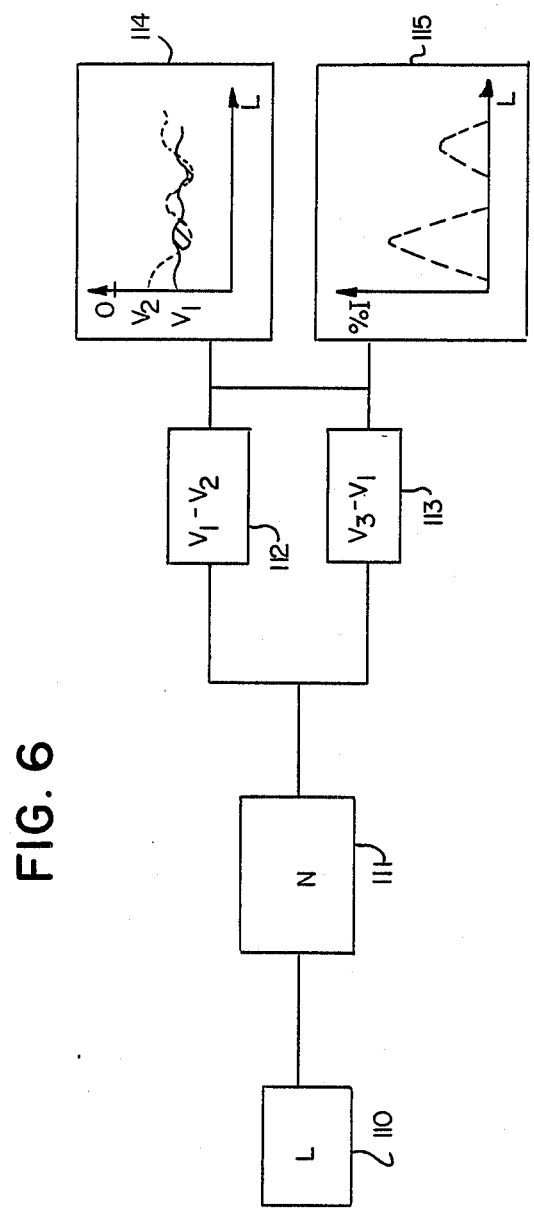
FIG. 6 is a diagram of the functions of the processing system in accordance with the invention.

The diagram of FIG. 6 illustrates the functions of the data-processing system, that is, the read-out at 110 of the recorded data, the standardization at 111 of the values V1, V2 and V3 on the basis of the values of the real potentials of the Cu/CuSO$_4$ electrodes utilized, which are measured off site, and the calculation at 112 and 113 of the differences V1−V2 and V3−V1. Elements 110, 111, 112 and 113 together comprise the data processing system which performs these calculations.

The values obtained for these differences permit the construction of curves 114 and 115 characterizing the anodic corrosion areas on the basis of the length of the buried pipe and the relative intensity of the corrosive effect of the soil and the environment on the buried pipe in each of these areas, respectively.

Figure 7:
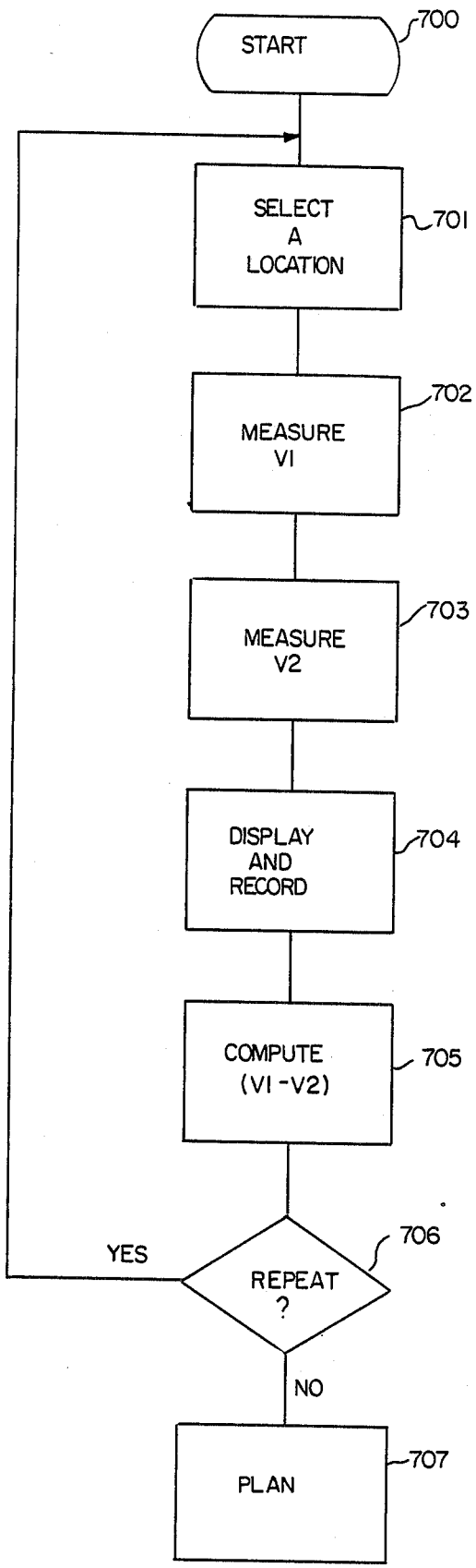
FIG. 7 is a flowchart of the method in accordance with the invention.

FIG. 7 is a flowchart of a method in accordance with the present invention. As shown therein, the method starts at step 700 in which the sensor is activated and then proceeds to step 701 in which a location is selected. The method then proceeds successively through step 702 in which V1 is measured, step 703 in which V2 is measured, step 704 in which the two measurements are displayed and recorded (see FIG. 6) and step 705 in which V1−V2 is computed. In step 706 it is determined whether an additional location is to be accessed. If so, the method returns to step 701, while if not, the method goes to step 707 in which the data is entered on a plan of the station.

The example which follows is intended to better illustrate the present invention without, however, limiting its scope.

EXAMPLE

Two corrosion surveys were conducted for one and the same TOTAL filling station of an expressway service facility. This station has six 60 m$^3$ tanks and a collector permitting the distribution of the fluids, which make up the buried metallic structures.

The first survey is a control survey and was carried out by the procedure known to those skilled in the art, which consists in measuring:

The potential difference V between the soil and the structure by means of a Cu/CuSO$_4$ electrode connected to a voltmeter which in turn is connected to the structure;

the resistivity $\rho$ of the soil in the vicinity of the structure, by means of a "Wenner bridge"; and the pH, with a pH meter, by core sampling of the soil in the vicinity of the structure.

Six measuring points were dealt with. The average values obtained for the measurements of V, $\rho$ and pH are as follows:

V=480 mV
$\rho$=2000 ohms/cm$^2$/cm
pH=6.2.

These results indicate an average soil situation in the vicinity of the structure corresponding to so-called "active" corrosion. Such corrosion generally calls for the application of cathodic protection to all structures.

The second set of test results was obtained over the entire structure with the method and apparatus of the invention.

For measuring $V_1$, $V_2$ $V_3$, a linear-development sensor having three Cu/CuSO$_4$ electrodes, as described in connection with FIGS. 3 and 4A, was used.

Analysis of the data relating to $V_1$, $V_2$ and $V_3$, measured on the site, that is, in the filling station, has made it possible to locate and size five corrosion areas for which the absolute value of $V_2$ is less than that of $V_1$, these five areas having later been marked on the plan of the station with different colors indicating the different intensities of the corrosive effect of the soil and the environment on the buried structure.

The results obtained by the method in accordance with the invention are summarized in the table which follows.

| Area | Length (cm) | White 0-25 | Green 25-50 | Orange 50-75 | Dark Red 75-100 |
|---|---|---|---|---|---|
| 1 | 80 | x | | | |
| 2 | 160 | | x | | |
| 3 | 10 | | | | x |
| 4 | 80 | | | x | |
| 5 | 10 | x | | | |

Relative intensity of corrosive effect in %

An intensity of the corrosive effect of 100% corresponds to a corrosion causing the start of leakage of the fluid stored in the structure at the level of the anodic area. It is seen that only one area, area 3, is highly corroded while areas 2 and 4 are moderately corroded and areas 1 and 5 are mildly corroded. On the basis of these results, it will be possible to take action at the level of the corroded areas of the structures buried in the ground at the station.

Contrary to the balance sheet of the first control survey, the corrosion figures obtained by the method of the invention permit to locate the anodic areas with a precision of a few centimeters and to quantify the risks of corrosion and leakage of product at their level.

What is claimed is:

1. A method of analyzing the corrosive effect of soil and environment on a buried metallic structure, which method comprises:
   (A) measuring at least two potential differences by means of at least one known reference-potential electrode placed in contact with the surface of the soil, the latter then forming the electrolyte and the buried structure forming a first metallic electrode, these potential differences being:
   a potential difference V1 between the at least one known reference-potential electrode on the soil surface and the buried structure that is equal to the sum of the potentials of the known reference-potential electrode, the buried-structure electrode, and a potential difference generated by electric cell formation occurring between the structure and the soil; and
   a potential difference V2 between the at least one known reference-potential electrode on the soil surface and the buried structure when the potential of that structure is returned to the soil surface by means of an electrical connection from the buried structure to a second metallic electrode resting on the soil surface in proximity to said known reference-potential electrode, this difference being equal to the sum of the potentials of the known reference-potential electrode and the second metallic electrode;
   (B) displaying and recording the potential differences with a data display and acquisition unit;
   (C) processing the data by means of a data-processing system for computing the difference (V1−V2) which is indicative of a corrosive effect of the soil and the environment on the buried structure; and
   (D) repeating said measuring at a plurality of locations on the soil surface to provide a plan of relatively corroded areas of said buried structure.

2. A method according to claim 1, wherein the known reference-potential electrode is an electrode of the Cu/CuSO$_4$ type.

3. A method according to claim 1, wherein the reference-potential electrode is placed at the vertical of a point being analyzed of the buried structure for measuring the potential difference V1.

4. A method according to claim 1, wherein the potential difference V2 is measured with a Cu/CuSO$_4$ electrode and said second metallic electrode secured thereto and placed on the soil surface at the same side of and at a horizontal distance d$_2$ from the vertical of a point being analyzed on the buried structure, d$_2$ ranging from 0 to 50 cm.

5. A method for analyzing the corrosive effect according to claim 1 applied to on site locating of anodic areas on said buried structure susceptible to corrosion, which method further comprises:
   measuring V1 and V2 repeatedly along the soil surface above the buried structure, which soil surface has first been moistened to assure contact between the soil and the sensor including said electrodes for measuring V1 and V2;
   reading the values of V1 and V2 on the display unit of the data display and acquisition unit; and
   locating and indicating the anodic areas when the absolute value of V1 is higher than that of V2.

6. A method according to claim 1, wherein said plurality of locations form a continuous path on the soil surface along which said potential differences are measured.

7. A method according to claim 1, wherein said plurality of locations are at discontinuous positions on the soil surface at which said potential differences are measured.

8. A method according to claim 1, wherein the potential differences that are measured further include at least a third potential difference V3 between the at least one known reference-potential electrode on the soil surface and the buried structure, wherein said third potential difference V3 is equal to the sum of the potentials of the known reference-potential electrode, the buried-structure electrode, and a modified potential difference generated by electric cell formation occurring between the buried structure and the soil, and wherein the processing further includes computing the difference (V3−V1).

9. A method according to claim 8, wherein the potential difference generated by the electric cell formation occurring between the buried structure and the soil is modified by generating at least one electric current between the Cu/CuSO$_4$ electrode and the buried-structure electrode before V3 is measured.

10. A method according to claim 8, wherein the potential difference generated by the electric cell formation between the buried structure and the soil is measured with a Cu/CuSO$_4$ electrode placed on the ground at a horizontal distance d$_3$ from the vertical of a point being analyzed on the buried structure, d$_3$ ranging from 50 cm to 2 meters.

11. An apparatus for analyzing the corrosive effect of soil and environment on a buried metallic structure, which apparatus comprises:
   a measuring system comprising a sensor comprising at least one Cu/CuSO$_4$ electrode to which a metallic electrode containing iron is secured, first means for connecting the Cu/CuSO$_4$ electrode to the buried metallic structure, second means for connecting the metallic electrode to the buried metallic structure by a selected one of a permanent and switchable electrical connection and at least one voltmeter, said measuring system being movable to provide measurements by said sensor at a plurality of locations on said soil surface;
   at least one data display and acquisition system consisting of at least one amplifier receiving a measurement from said measuring system, at least one analog-to-digital converter for converting an amplified output of said at least one amplifier, at least one magnetic recorder for recording a converted output of said at least one analog-to-digital converter and at least one display unit for the read-out on site of the output of a selected one of said at least one amplifier and said at least one analog-to-digital converter; and
   a system for the processing of these data comprising data-processing computing means for providing a signal at each said location indicative of a corrosive effect of the soil and environment on the buried structure and, based on the signals, a plan of relatively corroded areas of said buried structure.

12. An apparatus according to claim 11, wherein the measuring system further comprises at least one current generator.

13. An apparatus according to claim 11, wherein the measuring system comprises a point-to-point development sensor comprising at least one Cu/CuSO$_4$ electrode fabricated from a cylinder of an electrically passive, nonporous material and stoppered at its base with a plug of a porous material selected from the group consisting of wood, cork and a porous, electrically passive material, said cylinder containing a saturated solution of copper sulfate in which is immersed a copper rod providing for the electrical connection of said electrode, and a metallic electrode enveloping the Cu/CuSO$_4$ electrode as a metallic sheath.

14. An apparatus according to claim 13, wherein the metallic sheath is formed of low-carbon steel.

15. An apparatus according to claim 11, wherein the data processing by the data-processing computing means comprises standardizing values V1 and V2 on the basis of the real potentials of the Cu/CuSO$_4$ electrode or electrodes and computing a difference (V1−V2), wherein V1 is a potential difference between the soil surface and the buried metallic structure that is equal to the sum of the potentials of at least one known reference-potential electrode, the buried structure electrode and a potential difference generated by electric cell formation occurring between the structure and the soil, and V2 is a potential difference between the soil surface and the buried structure when the potential of that structure is returned, by means of an electrical connection, to said metallic electrode resting on the ground, this difference being equal to the sum of the potentials of the known reference-potential electrode and the metallic electrode.

16. An apparatus according to claim 15, wherein the data processing by the data-processing computer means further comprises computing a difference (V3−V1), wherein V3 is a potential difference between the at least one known reference-potential electrode on the soil surface and the buried structure that is equal to the sum of the potentials of said at least one known reference-potential electrode, the buried structure electrode and a modified potential difference generated by electrical cell formation occurring between the buried structure and the soil.

17. An apparatus according to claim 11, wherein the measuring system comprises a linear-development sensor comprising at least two Cu/CuSO$_4$ electrodes in the form of hollow wheels whose periphery forms the sensitive portion of the electrode, made from the group consisting of cork, wood, or an electrically passive, porous material, which electrodes have walls that are in the form of disks and are made of an electrically passive, nonporous material, and which electrodes contain copper disks having a diameter smaller than that of the wheel and contain a saturated solution of copper sulfate (CuSO$_4$), said electrodes being arranged physically in parallel and maintained integral with each other, one Cu/CuSO$_4$ electrode being at a first predetermined distance from the other, said linear development sensor further comprising said metallic electrode consisting of at least one disk.

18. An apparatus according to claim 17, wherein the measuring system further comprises at least a third Cu/CuSO$_4$ electrode, located at a second predetermined distance from said one Cu/CuSO$_4$ electrode.

19. An apparatus according to claim 17, wherein the metallic electrode is formed of low-carbon steel.

20. An apparatus according to claim 17, wherein the metallic electrode is connected to at least one of the Cu/CuSO$_4$ electrodes.

* * * * *